United States Patent
Malmstrom et al.

(10) Patent No.: US 6,636,010 B1
(45) Date of Patent: Oct. 21, 2003

(54) PRECISION DOSAGE APPARATUS, SYSTEM AND METHOD

(75) Inventors: James Malmstrom, Salt Lake City, UT (US); David Soss, Salt Lake City, UT (US)

(73) Assignee: Zevex, Inc., Salt Lake City ( * ) Notice: Subject to any disclaimer, the term of this patent is extended or adjusted under 35 U.S.C. 154(b) by 0 days.

(21) Appl. No.: 09/969,122

(22) Filed: Oct. 1, 2001

(51) Int. Cl.$^7$ .................................................. G05D 7/00
(52) U.S. Cl. ......................... 318/644; 318/11; 318/672; 318/362; 318/366; 604/65; 604/67; 604/123; 604/131; 417/36; 417/42; 417/44.1; 417/323; 417/321
(58) Field of Search .................. 318/3, 9–11, 638, 318/644, 671, 672, 757, 759, 362, 366, 375; 604/65, 67, 123, 131, 151; 417/22, 26, 18, 36, 42, 44.1, 44.11, 321, 323, 326, 63

(56) References Cited

U.S. PATENT DOCUMENTS

| | | | |
|---|---|---|---|
| 3,736,930 A | | 6/1973 | Georgi |
| 4,217,993 A | * | 8/1980 | Jess et al. ...................... 222/14 |
| 4,447,191 A | * | 5/1984 | Bilstad et al. ................. 417/12 |
| 4,469,481 A | * | 9/1984 | Kobayashi .................... 604/67 |
| 4,498,843 A | * | 2/1985 | Schneider et al. ............ 417/22 |
| 4,850,807 A | * | 7/1989 | Frantz .......................... 417/63 |
| 4,857,818 A | | 8/1989 | Hobbs ......................... 318/762 |
| 4,910,682 A | * | 3/1990 | Wolff et al. .................. 364/510 |
| 5,099,184 A | | 3/1992 | Hornung et al. ............. 318/375 |
| 5,244,463 A | * | 9/1993 | Cordner, Jr. et al. ........ 604/131 |
| 5,355,735 A | * | 10/1994 | Miller et al. .............. 73/861.05 |
| 5,395,320 A | | 3/1995 | Padda et al. |
| 5,538,405 A | | 7/1996 | Patno et al. ................. 417/326 |
| 5,630,710 A | * | 5/1997 | Tune et al. .................. 417/326 |
| 5,996,650 A | | 12/1999 | Phallen et al. |
| 6,030,359 A | | 2/2000 | Nowosielski |
| 6,121,739 A | | 9/2000 | Haberlander ................ 318/362 |

* cited by examiner

*Primary Examiner*—Bentsu Ro
*Assistant Examiner*—Rina I. Duda
(74) *Attorney, Agent, or Firm*—Randall B. Bateman

(57) ABSTRACT

A liquid dispensing system increases the precision, reliability, and safety of dispensing medications and other liquids. An electronic brake grounds a power terminal of a pump motor to absorb the kinetic energy of the motor and other mechanically coupled components. The electronic brake reduces overage and overage variation in the dispensing of liquids at very little cost or complexity. A watchdog circuit monitors a controller heartbeat signal and disables the motor in the absence of a regular beat. The watchdog circuit along with redundant power switches greatly reduce the possibility of motor runaway in the event of component failure. A controller begins or ends each dispensing cycle with a diagnostic which determines whether the liquid dispensing system is fully operational. If not, the controller may disable the motor, emit an alarm tone, and display an alarm message.

26 Claims, 5 Drawing Sheets

PRECISION DOSAGE APPARATUS, SYSTEM AND METHOD

BACKGROUND OF THE INVENTION

1. The Field of the Invention

The present invention relates generally to pumping control systems. More specifically, the invention relates to systems for controlling dispensing of medications to more accurately control dispensing of medication.

2. The Relevant Art

Medical science often requires that liquids be administered to a patient in a variety of situations. These liquids include simple intravenous feeding solutions, saline solutions for providing pressure to the eye during ocular surgery, contrast media infused to enhance imaging abilities, blood administered during transfusions, and nutrient solutions, medications, chemotherapy solutions, or the like delivered via intervenal or enteral means. In virtually all these applications, reliable and precise delivery of liquids is critical to successful treatment of the patient. In some applications, improper delivery of the liquids such as overrun may be life threatening to the patient.

Systems that are reliable and precise are often costly to design, manufacture and test. Indeed, the relative cost of medical care continues to increase often due to the increased cost of medical technology. Accordingly, within the health care industry there is a high need for low-complexity technology that is effective and reliable.

Overrun is particularly dangerous in medical applications in that even when detected, excessive delivery of a liquid often cannot be reversed. Overrun may be caused by hardware failures such as electronic switches being stuck in a certain state. Controller failures are also a problem in that processors are particular sensitive to environmental factors such as temperature and static. The firmware associated with a controller may contain logic errors or bad memory cells resulting in runaway programs that may "crash". Runaway or crashing programs may leave control circuitry stuck in a certain state such as in a pumping state where liquid is being delivered at a high rate.

In addition to reliability to prevent overrun and other errors associated with component failure, liquid dispensing systems need to be precise. Precise delivery facilitates the adjustment of dosages, to rates and levels that are optimum for treatment of the patient. Precision also facilitates consistency over time and between various devices and systems, a highly desirable feature in dosage systems.

Stepper motors are often used in applications that require precision. Unfortunately stepper motors require complex control signals that must be properly phased to advance the motor. Stepper motors are also often costly and difficult to test.

Standard motors such as induction motors are typically low cost but suffer from lack of precision in that motors often freewheel after power is cut off. Freewheeling results in liquid overage and overage variability in that the duration and speed of freewheeling is affected by environmental and usage factors such as temperature and motor speed.

Accordingly, what is needed is a liquid dispensing control system for standard motors that is low-cost, and reliable, and that eliminates freewheeling and prevents overrun in the event of system failures.

OBJECTS AND BRIEF SUMMARY OF THE INVENTION

The apparatus of the present invention has been developed in response to the present state of the art, and in particular, in response to the problems and needs in the art that have not yet been fully solved by currently available liquid dispensing systems. Accordingly, it is an overall object of the present invention to provide an improved method, apparatus and system for dispensing liquids that overcomes many or all of the above-discussed shortcomings in the art.

In particular, it is an object of the present invention to provide a control system for a liquid dispensing system that is low-cost, reliable, eliminates or reduces freewheeling, and substantially prevents overrun in the event of system failures.

These and other objects of the invention are realized in a control system for a liquid dispensing system which includes an electronic brake to stop motor freewheeling, power and ground switches to reliably control the motor, and a watchdog circuit to monitor the controller and disable the motor in the event of system failures.

In accordance with a first aspect of the invention, the electronic brake grounds a power terminal of the motor in response to a stop signal. Grounding the power terminal creates a braking effect as kinetic energy from mechanical inertia is converted to electromagnetic energy within the windings of the motor. The brake in turn absorbs the electromagnetic energy to greatly reduce or eliminate freewheeling. In essence, the motor momentarily acts as a generator allowing the brake to quickly absorb and stop the kinetic energy present in the dosage delivery system.

In accordance with a second aspect of the invention, redundant switches, one to connect to power and the other to connect to ground, ensure that the failure of a switch does not result in the motor being stuck in a running state.

In accordance with a third aspect of the invention, a watchdog circuit monitors a controller heartbeat signal to ensure that the controller is reliably providing a valid 'beat' at an acceptable rate. If so, the watchdog asserts an enable signal which activates one of the switches that control power to the motor. If the required conditions are not met, the watchdog de-asserts the enable signal placing a switch in a non-conductive state, thus disabling the motor and preventing the possibility of overrun.

In accordance with a fourth aspect of the invention, a controller starts or ends each dispensing cycle with a diagnostic which determines whether the liquid dispensing system is fully operational. If not, the controller may perform shutdown operations such as disabling the motor along with error indication operations such as emitting an alarm tone and displaying an alarm message.

To achieve the foregoing objects, and in accordance with the invention as embodied and broadly described herein in the preferred embodiments, an apparatus, method and system for delivery of liquids is described that is reliable, precise and low-cost.

BRIEF DESCRIPTION OF THE DRAWINGS

In order that the manner in which the advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow. Additionally, it should be understood that not all embodiments made in accordance with aspects of the present invention will necessarily achieve all objects of the invention.

Figure 1:
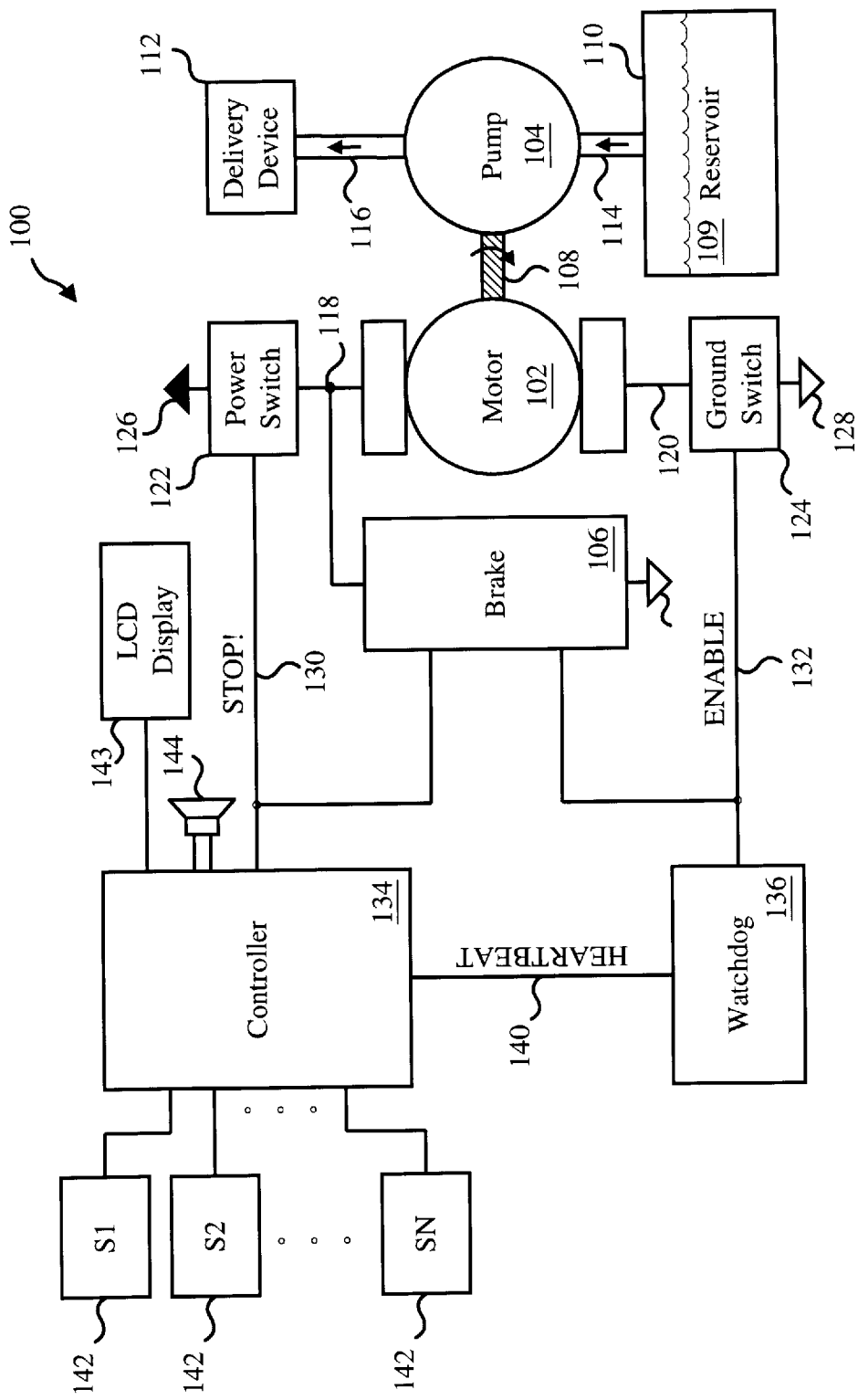
FIG. 1 is a block diagram of a dosage delivery system in accordance with the present invention.

FIG. 1 shows a dosage delivery system 100 of the present invention. In the depicted embodiment the dosage delivery system 100 includes a motor 102, a pump 104, and a brake 106. The motor 102 is mechanically coupled to the pump 104 via a coupler 108. In one embodiment, the coupler 108 is a screw-type drive shaft tangential to an eccentric gear of the pump 104. In the preferred embodiment, the motor 102 is a DC motor, the pump 104 is a peristaltic pump and the coupler 108 provides a very low gear ratio to increase precision. A peristaltic pump is preferred in that it facilitates precise delivery of liquids at a low cost.

The motor 102 drives the pump 104 which in turn pumps a liquid 109 from a reservoir 110 to a delivery device 112. The liquid 109 may travel through a supply tube 114 to the pump 104 and further through a delivery tube 116 to the delivery device 112. In certain embodiments, for example with some peristaltic pumps, the supply tube 114 and the delivery tube 116 are the same tube.

In the depicted embodiment, the motor 102 is electrically connected to a power terminal 118 and a ground terminal 120. The power terminal 118 and the ground terminal 120 provide a DC voltage to the motor 102 as controlled by a power switch 122 and a ground switch 124. When the power switch 122 and the ground switch 124 are both in a conductive state, DC power is supplied to the motor 102 from a power bus 126 and a ground bus 128. The motor 102 drives the pump 104. When either switch is in a non-conductive state no power is supplied to the motor 102. Requiring both switches to be in a conductive state prevents the possibility of runaway pumping in the event of the failure of a switch.

Due to a variety of factors, removing the supply of power to the motor 102 may not result in immediate stoppage of the pump 104 resulting in overage in the delivery of the liquid 109. For example, the motor 102 may have inductive energy stored within various windings. The motor 102, the pump 104, and the coupler 108 may have some mechanical inertia. The amount of overage may be inconsistent and dependent on a variety of electrical, mechanical and environmental factors that vary from system to system and are highly dependent upon usage patterns.

To address the problem of overage and inconsistent overage, the brake 106 of the present invention more quickly stops the motor 102 resulting in greater delivery precision. In the depicted embodiment, the brake 106 grounds the power terminal 118. Grounding the power terminal 118 removes any electromagnetic energy present within the windings of the motor 102. More particularly, grounding the power terminal 118 creates a braking effect as mechanical kinetic energy from inertia is converted to electromagnetic energy within the windings of the motor 102 which is absorbed by the brake 106. In essence, the motor 102 momentarily acts as a generator allowing the brake 106 to quickly absorb and stop the kinetic energy present in the dosage delivery system 100.

In the depicted embodiment, the brake 106 receives a stop signal 130 and a enable signal 132. In several of the Figures, the 'STOP!' label corresponding to the stop signal 130 is appended with an exclamation point indicating that the signal is asserted with a low voltage rather than a high voltage. In addition to the brake 106, the stop signal 130 is also received by the power switch 122, while the enable signal 132 is also received by the ground switch 124. Using separate signals to control the power switch 122 and the ground switch 124 increases the reliability of the present invention. In the depicted embodiment, the stop signal 130 is provided by a controller 134 while a watchdog 136 provides the enable signal 132.

As depicted in FIG. 1, the controller 134 provides a heartbeat signal 140 to the watchdog 136. The heartbeat signal indicates that the controller is in a healthy active state. The watchdog 136 monitors the heartbeat signal 140 to ensure that the controller 134 is reliably providing a valid 'beat' at an acceptable rate. If so, the watchdog asserts the enable signal 132. If the required conditions are not met, the watchdog 136 de-asserts the enable signal 132 placing the ground switch 124 in a non-conductive state, thus disabling the motor 102 and the pump 104.

In addition to providing the stop signal 130 and the heartbeat signal 140, the controller 134 receives signals from a number of sensors 142. The sensors 142, include for example pressure sensors, temperature sensors, motor sensors and the like. The sensors 142 provide the controller 134 with information that is useful and essential to ensure that the dosage delivery system 100 is operating accurately and reliably. In the preferred embodiment, the sensors 142 include a dosage sensor that provides information on rotational movement in the motor 102 or the pump 104. The dosage sensor may be an emitter-detector pair aligned perpendicular to a rotational surface with alternating dark and light regions.

The controller 134 may also provide signals to control a visual indicator 143, such as an LCD display, and an audio indicator 144, for example a speaker. The visual indicator 143 and the audio indicator 144 facilitate the rendering of information such as battery levels, fluid levels, flow rates, error conditions, alarms and the like.

Figure 2A:
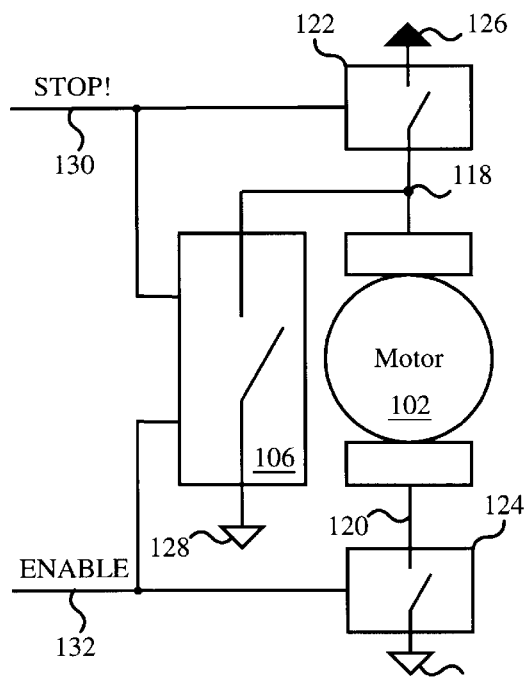
FIG. 2a is a block diagram highlighting control circuitry associated with the motor in accordance with the present invention.

FIGS. 2a–2d contain several schematic block diagrams of control circuitry associated with the motor 102. As depicted in FIG. 2a, the brake 106 is essentially a grounding switch which is activated under control of the stop signal 130 and the enable signal 132. The stop signal 130 and the enable signal 132 also control the power switch 122 and the ground switch 124. In the preferred embodiment, the brake 106 need only be activated when the enable signal 132 is asserted (indicating that the motor 102 is potentially on), followed by assertion of the stop signal 130. In this scenario, asserting the stop signal places the power switch 122 in a non-conductive state, thereby cutting off power to the motor 102. Furthermore, the brake 106 is placed in a conductive state thereby absorbing the kinetic energy of the mechanical components as previously described.

Figure 2B:
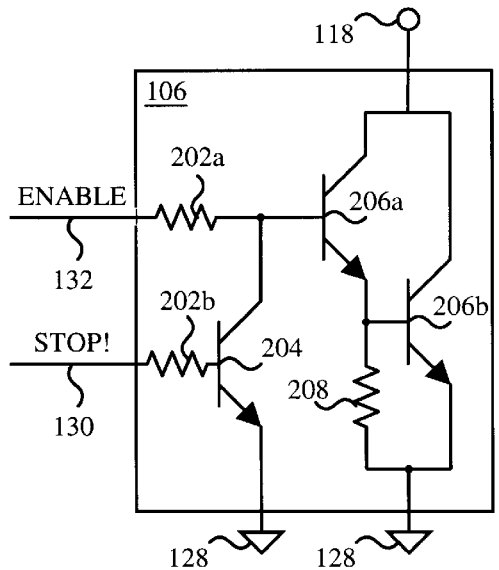
FIG. 2b is a schematic diagram showing a first embodiment of a brake in accordance with the present invention.
Figure 2C:
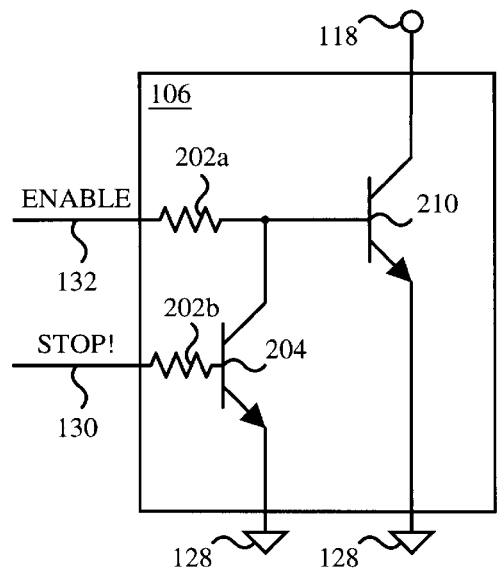
FIG. 2c is a schematic diagram showing a second embodiment of a brake in accordance with the present invention.
Figure 2D:
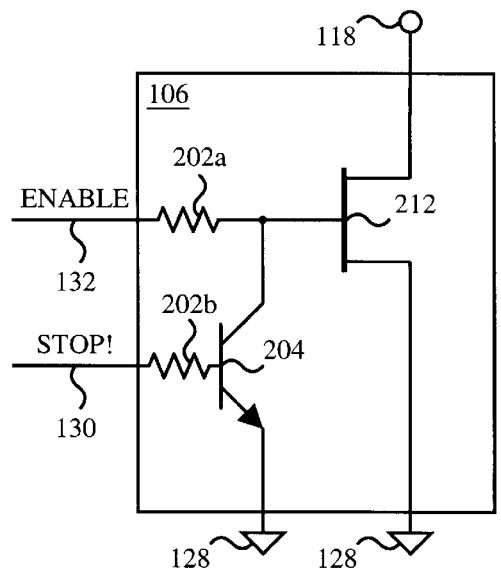
FIG. 2d is a schematic diagram showing a third embodiment of a brake in accordance with the present invention.

FIGS. 2b, 2c, and 2d show various embodiments of the brake 106 that are placed in a conductive state when both the enable signal 132 and the stop signal 130 are asserted. Referring to FIG. 2b, a pair of isolation resistors 202a and 202b isolate the enable signal 132 and the stop signal 130 from circuitry internal to the brake 106. The isolation resistor 202a allows an asserted enable signal 132 to provide current to either an anding transistor 204 or a darlington pair 206 depending on the state of the stop signal 130. When the stop signal 130 is not asserted, the anding transistor 204 absorbs any current provided by the asserted enable signal 132 thus turning off the darlington pair 206 and placing the brake 106 in a non-conductive state.

When the enable signal 132 is not asserted (i.e. at a low voltage), current through the isolation resistor 202a pulls the input the transistor 206a toward ground resulting in little or no current being drawn from the power terminal 118. Likewise, when the stop signal is not asserted (i.e. at a high voltage) the anding transistor 204 is turned on which also results in the input of the transistor 206a being pulled toward ground. The combination of the anding transistor 204 and the isolation resistor 202a effectively create an 'AND' gate. Only by asserting both the enable signal 132 and the stop signal 130 simultaneously will the brake 106, as depicted in FIG. 2a, absorb current (other than leakage current) from the power terminal 118.

The transistors 206a and 206b that comprise the darlington pair 206 facilitate a potentially large current draw on the power terminal 118. A large current draw allows the brake 106 to absorb considerable energy from the power terminal 118 and therefore the motor 102. A leakage resistor 208 absorbs any leakage current from the transistor 206a.

Figure 3A:
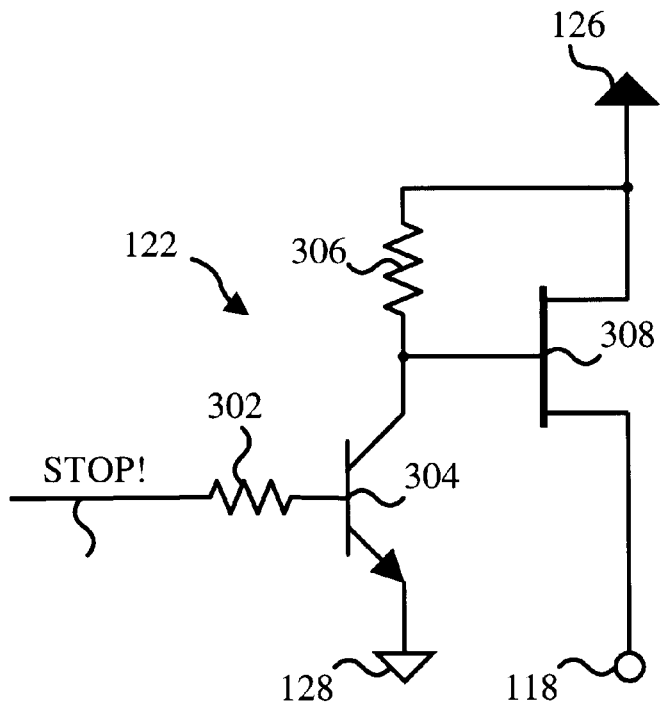
FIG. 3a is a schematic diagram showing one embodiment of a power switch in accordance with the present invention.
Figure 3B:
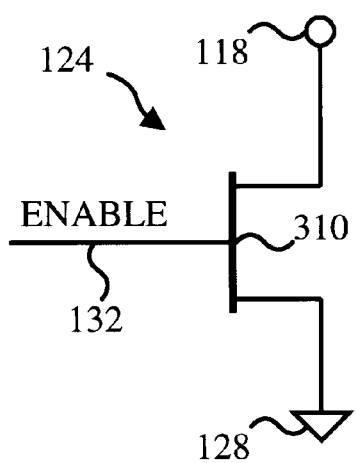
FIG. 3b is a schematic diagram showing a first embodiment of a ground switch in accordance with the present invention.
Figure 3C:
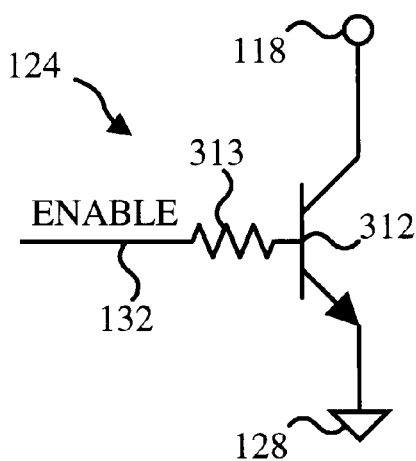
FIG. 3c is a schematic diagram showing a second embodiment of a ground switch in accordance with the present invention.

Referring to FIGS. 2c and 2d, alternative embodiments of the brake 106 replace the darlington pair 206 and the leakage resistor 208 with a single transistor 210 or a FET 212. Otherwise, the embodiments depicted in FIGS. 2c and 2d are identical to the embodiment depicted in FIG. 2b. Using the single transistor 210 may be preferred in situations where little current need be absorbed from the power terminal 118 and the motor 102. The FET 212 may be desirable in applications requiring the brake 106 to provide good isolation (i.e. a very low leakage current) when in a non-conductive state. FIGS. 3a–3c show several schematic block diagrams which focus on the power switch 122 and the ground switch 124. Referring to FIG. 3a, one embodiment of the power switch 122 includes an isolation resistor 302, an inverting transistor 304, a pull-up resistor 306 and a FET 308. The various components of the power switch 122 work together to place the power switch 122 in a conductive or non-conductive state depending on whether the stop signal 130 is asserted.

When the stop signal 130 is asserted (i.e. at a low voltage), the isolation resistor 302 is pulled toward ground thus turning off the inverting transistor 304. In this condition, the pull-up resistor 306 raises the voltage on the gate of the FET 308. In the preferred embodiment, the FET 308 is a p-channel MOSFET and a high voltage places the FET 308 in a non-conductive state thus cutting off power to the power terminal 118 and disabling the motor 102.

In those situations in which the stop signal 130 is not asserted (i.e. at a high voltage), the isolation resistor 302 pulls the gate of the inverting transistor 304 toward power causing the inverting transistor 304 to turn on. In this condition, the inverting transistor 304 pulls the voltage on the gate of the FET 308 toward ground. In the preferred embodiment, the FET 308 is a p-channel MOSFET and a low voltage places the FET 308 in a conductive state thus providing power from the power bus 126 to the power terminal 118, and thereby the motor 102.

Referring to FIG. 3b, a first embodiment of the ground switch 124 is comprised solely by a FET 310 which is preferably an n-channel MOSFET. When the enable signal 132 is asserted (i.e. at a high voltage) the FET 310 is placed in a conductive state. In a conductive state, the ground terminal 120 and the ground bus 128 are electrically tied together allowing a return or grounding path for current in the motor 102. In contrast, when the enable signal 132 is not asserted (i.e. at a low voltage) the FET 310 is placed in a non-conductive state, the ground terminal 120 and the ground bus 128 are electrically isolated resulting in no return or grounding path for current in the motor 102. As used within the dosage delivery system 100 depicted in FIG. 1, not asserting the enable signal 132 effectively disables the motor 102.

Referring to FIG. 3c, a second embodiment of the ground switch 124 similar to FIG. 3b, includes a transistor 312 and an isolation resistor 313. When the enable signal 132 is asserted (i.e. at a high voltage), the transistor 312 is turned on allowing current to flow from the ground terminal 120 to the ground bus 128. When the enable signal 132 is not asserted (i.e. at a low voltage) the transistor 312 is turned off thereby electrically isolating the ground terminal 120 and the ground bus 128.

Figure 4:
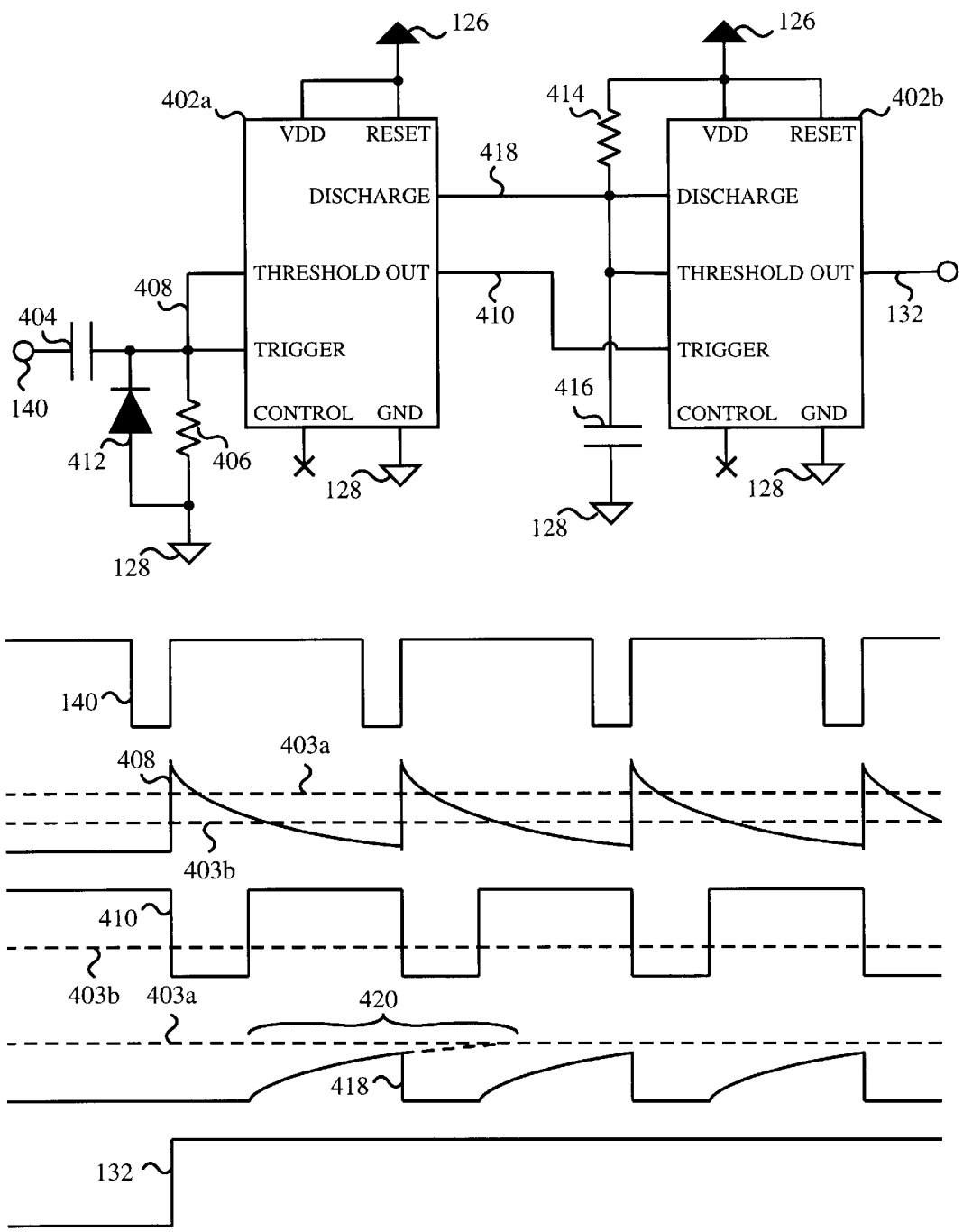
FIG. 4 is a schematic diagram and associated timing diagram depicting one embodiment of a watchdog in accordance with the present invention.

Referring to FIG. 4, the watchdog 136 may include a pair of timers 402a and 402b. The timers 402a and 402b detect whether the heartbeat signal is reliably providing a valid 'beat' at an acceptable rate. As depicted, the timers 402a and 402b are essentially RS flip-flops that are reset when the voltage on the threshold input is greater than a threshold voltage 403a and set when the voltage on the trigger input is less than a trigger voltage 403b. In one embodiment, the timers 402a and 402b are 555 timers, the threshold voltage 403a is $\frac{2}{3}$rds the supply voltage, and the trigger voltage 403b is $\frac{1}{3}$rd the supply voltage. The timer 402a detects a valid beat from the heartbeat signal 140, while the timer 402b ensures that the detected beats occur at an acceptable rate. Timing is controlled by RC circuits external to the timers 402a and 402b.

A rising edge of the heartbeat signal 140 is passed by a high pass filter consisting of a high pass capacitor 404 and a discharging resistor 406. The rising edge produces a voltage on an input 408 sufficient enough to reset the output of the timer 402a and thereby provide a beat detected signal 410 (the beat detected signal 410 is asserted with a low voltage). The discharging resistor 406 eventually bleeds off the input 408 resulting in de-assertion of the beat detected signal 410. A diode 412 provides input protection to the timer 402a.

The beat detected signal 410 is tied to the trigger input of the timer 402b. Asserting the beat detected signal 410 sets the output of the timer 402b thereby asserting the enable signal 132. In addition to asserting the enable signal 132, timer 402b discontinues discharging a timing capacitor 416. The enable signal 132 remains set until current from a charging resistor 414 charges a timing signal 418 beyond a certain threshold which in one embodiment is ⅔rds the supply voltage.

Continuing to refer to FIG. 4, the timing capacitor 416 and the charging resistor 414 determine the length of a heartbeat window 420. As long as the beat detected signal 410 is asserted within the heartbeat window 420, the enable signal 132 will remain asserted. The enable signal 132 is used within the dosage delivery system 100 depicted in FIG. 1 to enable and disable the motor 102 via the ground switch 124. As depicted in FIG. 1, the enable signal 132 also enables the brake 106.

Figure 5A:
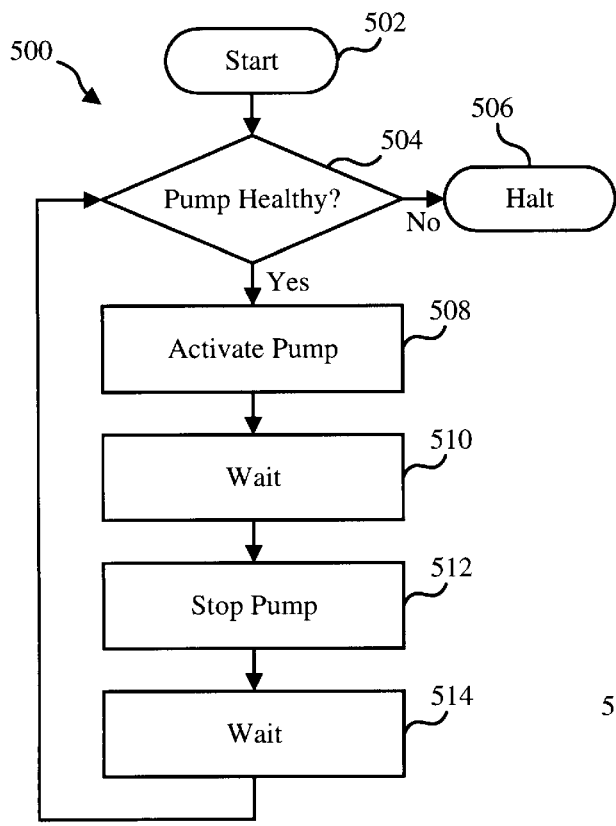
FIG. 5a is a flow chart of a liquid dispensing method in accordance with the dosage delivery system of the present invention.

Referring to FIG. 5a, a liquid dispensing method 500 of the present invention is shown that may be performed in conjunction with the dosage delivery system 100. The liquid dispensing method 500 starts 502, and proceeds immediately to a diagnostic 504. In one embodiment, the diagnostic 504 ascertains whether the dosage delivery system 100 is functioning properly. If not, the method proceeds to a halt 506.

In conducting the halt 506, the liquid dispensing method 500 may perform shutdown operations such as disabling the motor 102, as well as error indication operations such as emitting an alarm tone through the audio indicator 144 and displaying an alarm message through the visual indicator 143. If the diagnostic determines that the system is functioning properly, the liquid dispensing method 500 continues to an activate 508.

The activate 508, activates the dispensing of liquid. In one embodiment, activating the dispensing of liquid includes de-asserting the stop signal 130, providing a valid beat on the heartbeat signal 140, and sensing that the motor 102 is active. The activate 508 is followed by a wait 510. The wait 510 delays the execution of a stop 512 until an appropriate amount of liquid 109 has been dispensed. The wait 510 may be performed in a variety manners including without limitation scheduling a timer interrupt, polling a timer, polling a dispensing meter, waiting for a hardware signal and the like. In the preferred embodiment the wait 510 includes monitoring a dosage sensor that provides information on the amount of liquid being dispensed. In one embodiment, the wait 510 also includes providing a valid beat on the heartbeat signal 140 at regular intervals.

The stop 512 generally stops all activity commenced by the activate 508. In particular the stop 512 discontinues dispensing of the liquid 109. In one embodiment, the stop 512 asserts the stop signal 130 and discontinues providing a valid beat on the heartbeat signal 140. In the preferred embodiment, asserting the stop signal 130 causes the brake 106 to ground the power terminal 118 resulting in electro-magnetic braking of the pump 104. After the stop 512, the liquid dispensing method 500 proceeds to a sleep 514.

The sleep 514 delays further processing of the liquid dispensing method 500 until further processing is needed. In one embodiment, the sleep 514 includes placing the controller 134 in a low-power standby mode, scheduling a timer interrupt, and resuming normal processing in response to the timer interrupt. After the sleep 514 is completed, the liquid dispensing method 500 returns to the diagnostic 504. Assuming the diagnostic 504 yields favorable results as described above, the liquid dispensing method 500 may loop indefinitely.

Figure 5B:
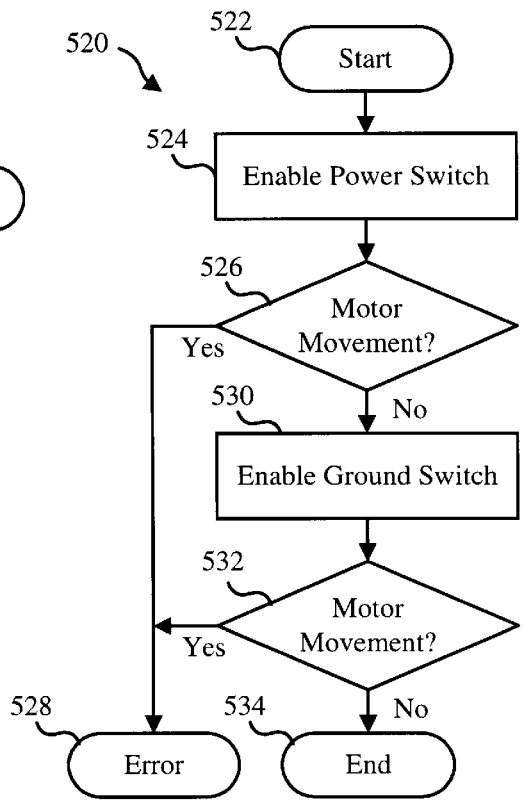
FIG. 5b is a flow chart of a diagnostic method in accordance with the dosage delivery system of the present invention.

Referring to FIG. 5b, a diagnostic method 520 may be performed in accordance with the dosage delivery system 100 and the liquid dispensing method 500. In one embodiment the diagnostic method 520 is performed as the diagnostic 504 of the liquid dispensing method 500. The diagnostic method 520 tests critical elements of the dosage delivery system 100. In the preferred embodiment, the diagnostic method 520 tests circuitry used to control the motor 102.

The diagnostic method 520 commences with a start 522, followed by an enable power switch 524. In the preferred embodiment, the enable power switch 524 occurs by discontinuing a valid beat on the heartbeat signal 140, and de-asserting the stop signal 130. De-asserting the stop signal 130 should place the power switch 122 in a conductive state and thereby provide power to the motor 102. However, discontinuing a valid beat on the heartbeat signal 140 causes the enable signal 132 to be de-asserted which should result in the ground switch 124 being placed in a non-conductive state and the motor 102 being disabled.

The diagnostic method 520 proceeds from the enable power switch 524 to a first motor test 526 which ascertains if the motor 102 is actually running. If so, a problem exists in the control circuitry associated with the motor 104 and the diagnostic method 520 proceeds to an error 528 and terminates. In one embodiment, the error 528 performs error indication operations such as emitting an alarm tone through the audio indicator 144 and displaying an alarm message through the visual indicator 143.

As depicted in FIG. 5b, the diagnostic method 520 proceeds from the first motor test 526 to an enable ground switch 530. In the preferred embodiment, the enable ground switch 530 occurs by asserting the stop signal 130 and providing a valid beat on the heartbeat signal 140. Providing a valid beat on the heartbeat signal 140 should result in the ground switch 124 being placed in a conductive state thus providing a return path for power to the motor 102. However, asserting the stop signal 130 should result in the power switch 122 being placed in a non-conductive state and the motor 104 being disabled.

The enable ground switch 530 is followed by a second motor test 532 which in one embodiment is identical to the first motor test 526 and ascertains whether the motor 102 is running. If so, a problem exists in the control circuitry associated with the motor 102 and the diagnostic method 520 proceeds to the error 528 and terminates. Otherwise, the diagnostic method 520 proceeds to an end 534 where the method terminates.

Figure 5C:
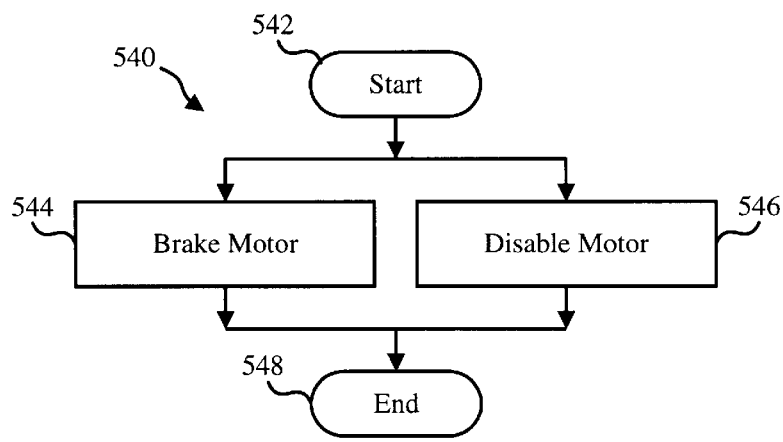
FIG. 5c is a flow chart of a stop method in accordance with the dosage delivery system of present invention.

FIG. 5c shows one embodiment of a stop method 540 in accordance with the dosage delivery system 100 and the liquid dispensing method 500. In one embodiment, the stop method 540 is performed as the stop 512 step of the liquid dispensing method 500. In the preferred embodiment, the stop method 540 facilitates stopping the motor 102 by converting kinetic energy to electromagnetic energy in the motor 102 and absorbing the electromagnetic energy with the brake 106.

The stop method 540 begins with a start 542 and proceeds concurrently to a brake 544, and a disable motor 546. The brake motor 544 and the disable motor 546 need not occur simultaneously. In the preferred embodiment, the staging of the brake motor 544 and the disable motor 546 is tuned to result in the least variation in stoppage of the motor 102.

In the preferred embodiment, the brake motor 544 engages the brake 106 to absorb electromagnetic energy from the windings of the motor 102. In one embodiment, engaging the brake 106 grounds the power terminal 118. In that same embodiment, the disable motor 546 places the power switch 122 in a non-conductive state thus isolating the power bus 126 from the power terminal 118 and cutting off power to the motor 102. After completion of the brake motor 544 and the disable motor 546, the stop method 540 proceeds to an end 548 whereupon the method terminates.

In conjunction with the stop method 540, the liquid dispensing method 500, and the dosage delivery system 100, it is worth mentioning the advantage of cutting off power and absorbing electromagnetic energy from the windings of the motor 102. Cutting power and absorbing electromagnetic energy from the windings of the motor 102 results in efficient stoppage of the motor 102 including the dissipation of kinetic energy in the dosage delivery system 100. Tuning the relative timing of engaging the brake 106 and disabling the motor 102 facilitates reducing overage in the delivery of the liquid 109. Furthermore, the faster stoppage achieved by these methods helps minimize system and usage dependent variations in overage. The result is increased precision for the dosage delivery system 100.

The present invention may be embodied in other specific forms without departing from its spirit or essential characteristics. The described embodiments are to be considered in all respects only as illustrative and not restrictive. The scope of the invention is, therefore, indicated by the appended claims rather than by the preceding description. All changes, which come within the meaning and range of equivalency of the claims, are to be embraced within their scope.

What is claimed is:

1. An apparatus for delivering a dosage of a liquid, the apparatus comprising:
    a peristaltic pump configured to pump a liquid;
    a pumping motor mechanically coupled to the peristaltic pump;
    a power terminal configured to provide power to the pumping motor; and
    a momentary brake configured to receive a stop signal, momentarily ground the power terminal, and then cease grounding of the power terminal, all in response to the stop signal.

2. The apparatus of claim 1, further comprising a power switch and a ground switch configured to control power to the pumping motor.

3. The apparatus of claim 2, further comprising a watchdog circuit configured to monitor a heartbeat signal and disable the pumping motor in response to irregularities in the heartbeat signal by sending a signal from the watchdog circuit directly to the pumping motor, regardless of commands being received from a control processor.

4. The apparatus of claim 3, wherein the watchdog circuit is configured to disable the pumping motor by opening a power switch or a ground switch.

5. The apparatus of claim 3, further comprising a controller configured to provide the heartbeat signal.

6. The apparatus of claim 5, further comprising a motor sensor configured to provide motor activity information to the controller.

7. The apparatus of claim 6, further comprising an audible alarm operably connected to the controller.

8. A system for controlling delivery dosage, the system comprising:
    a reservoir configured to hold a liquid;
    a delivery device configured to receive the liquid;
    a peristaltic pump configured to pump the liquid from the reservoir to the delivery device;
    a pumping motor mechanically coupled to the peristaltic pump;
    a power terminal configured to provide power to the pumping motor; and
    a momentary broke configured to receive a stop signal, momentarily ground the power terminal, and then cease grounding of the power terminal, all in response to the stop signal.

9. The system of claim 8, further comprising a power switch and a ground switch configured to control power to the pumping motor.

10. The apparatus of claim 9, further comprising a watchdog circuit configured to monitor a heartbeat signal and disable the pumping motor in response to irregularities in the heartbeat signal by sending a signal from the watchdog circuit directly to the pumping motor, regardless of commands being received from a control processor.

11. The apparatus of claim 10, wherein the watchdog circuit is configured to disable the pumping motor by opening the ground switch or the power switch.

12. The apparatus of claim 10, further comprising a controller configured to provide the heartbeat signal.

13. The apparatus of claim 12, further comprising a motor sensor configured to provide motor activity information to the controller.

14. The apparatus of claim 13, further comprising an audible alarm operably connected to the controller.

15. A method for controlling a dosage delivery system, the method comprising:
    activating a pumping motor;
    waiting until a desired dosage is delivered; and
    momentarily grounding power to the pumping motor to stop further movement thereof, thereby conserving energy by not continuously grounding power.

16. The method of claim 15, wherein waiting comprises monitoring a dosage sensor.

17. The method of claim 15, further comprising repeating delivery of the desired dosage at regular intervals.

18. The method of claim 17, further comprising testing the pumping motor and associated control circuitry.

19. The method of claim 17, further comprising disabling the pumping motor upon particular testing errors.

20. The method of claim 17, wherein the method further comprises monitoring a motor sensor while independently activating a power switch and a grounding switch, the power switch and the grounding switch configured to control power to the pumping motor.

21. A method for controlling a dosage delivery system, the method comprising:
    activating a pumping motor so as to move a peristaltic pumping mechanism a desired distance; and
    momentarily grounding power to the pumping motor to stop further movement of the peristaltic pumping mechanism, thereby conserving energy by not continuously grounding a power.

22. The method of claim 21, wherein testing comprises monitoring a motor sensor while independently activating a power switch and a grounding switch, the power switch and the grounding switch configured to control power to the pumping motor.

23. A method for controlling a dosage delivery system, the method comprising:

activating a pumping motor so as to move a peristaltic pumping mechanism a desired distance and developing a controller heartbeat signal having a regular beat; and disabling the pumping motor in the absence of a regular beat by sending a signal from a watchdog circuit directly to the pumping motor, regardless of commands being received from a control processor.

24. An apparatus for delivering a dosage of a liquid, the apparatus comprising:

a peristaltic pump configured to pump a liquid, the peristaltic pump comprising a pumping motor; and a momentary break configured to receive a stop signal, momentarily ground the pumping motor, and then cease grounding the pumping motor, all in response to the stop signal.

25. The apparatus of claim 24, further comprising a power switch and a ground switch configured to control power to the pumping motor.

26. An apparatus for delivering a dosage of a liquid, the apparatus comprising:

a peristaltic pump configured to pump a liquid, the peristaltic pump comprising a pumping motor;

means for developing a heartbeat signal; and a watchdog circuit configured to monitor a heartbeat signal and disable the pumping motor in response to irregularities in the heartbeat signal by sending a signal from the watchdog circuit directly to the pumping motor, regardless of commands being received from a control processor.

* * * * *